(12) United States Patent
Cadwalader et al.

(10) Patent No.: US 7,591,590 B2
(45) Date of Patent: *Sep. 22, 2009

(54) RADIATION ATTENUATION SYSTEM

(75) Inventors: John A. Cadwalader, Overland Park, KS (US); William W. Orrison, Las Vegas, NV (US)

(73) Assignee: Worldwide Innovations & Technologies, Inc., Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/949,568

(22) Filed: Dec. 3, 2007

(65) Prior Publication Data

US 2008/0075224 A1     Mar. 27, 2008

Related U.S. Application Data

(63) Continuation of application No. 10/999,116, filed on Nov. 29, 2004, now Pat. No. 7,303,334, which is a continuation-in-part of application No. 10/808,731, filed on Mar. 25, 2004, now Pat. No. 7,099,427.

(51) Int. Cl.
*H01J 35/16* (2006.01)
*G21F 3/00* (2006.01)

(52) U.S. Cl. ............................ 378/203; 378/4; 378/204; 250/519.1

(58) Field of Classification Search ............. 378/4, 378/19, 20, 117, 203, 204, 208, 210; 250/515.1–517.1, 250/519.1

See application file for complete search history.

(56) References Cited

U.S. PATENT DOCUMENTS

| | | | |
|---|---|---|---|
| 2,794,128 A | 5/1957 | Shasky | |
| 3,419,006 A | 12/1968 | King | |
| 3,432,657 A | 3/1969 | Slavin | |

(Continued)

FOREIGN PATENT DOCUMENTS

FR    2 439 460    10/1978

OTHER PUBLICATIONS

Promotional material titled Xenolite Radiation Protection Garments by DuPont Technology "Less Weight . . . Full Protection," Manufactured by Lite Tech. Inc., 18 Depot Street, Bridgeport, PA 19405, updated (6 sheets).

*Primary Examiner*—Edward J Glick
*Assistant Examiner*—Thomas R Artman
(74) *Attorney, Agent, or Firm*—Foley & Lardner LLP

(57) ABSTRACT

A radiation attenuation system for use with Computed Tomography procedures and a Computed Tomography having a radiation attenuation system are disclosed. The radiation attenuation system includes a shield made of a flexible radiation attenuation material and an interface supporting the shield at the Computed Tomography machine. The interface allows the shield to be selectively added to and removed from the Computed Tomography machine. The disclosed Computed Tomography machine includes a gantry defining an opening through which a patient table is at least partially inserted during a Computed Tomography procedure and a housing enclosing the gantry without substantially covering the opening and remaining fixed relative thereto. The housing is at least partially defined by a front panel that is formed of a substrate and a radiation attenuation material. The radiation attenuation material is in the form of a flexible sheet and is fixed relative to the substrate. The radiation attenuation material attenuates radiation that would otherwise pass through the front panel during the Computed Tomography procedure.

21 Claims, 9 Drawing Sheets

U.S. PATENT DOCUMENTS

| | | | |
|---|---|---|---|
| 3,514,607 A | 5/1970 | Webster | |
| 3,935,099 A | 1/1976 | Weaver et al. | |
| 3,980,889 A | 9/1976 | Haas et al. | |
| 4,062,518 A * | 12/1977 | Stivender et al. | 250/519.1 |
| 4,196,355 A | 4/1980 | Maine | |
| 4,286,170 A | 8/1981 | Moti | |
| 4,581,538 A | 4/1986 | Lenhart | |
| 4,621,808 A | 11/1986 | Orchard et al. | |
| 4,670,658 A | 6/1987 | Meyers | |
| 4,852,141 A | 7/1989 | Horn | |
| 4,938,233 A | 7/1990 | Orrison, Jr. | |
| 4,977,585 A * | 12/1990 | Boyd | 378/4 |
| 5,006,718 A * | 4/1991 | Lenhart | 250/519.1 |
| 5,038,047 A | 8/1991 | Still | |
| 5,097,497 A | 3/1992 | Deucher et al. | |
| 5,247,182 A | 9/1993 | Servant et al. | |
| 5,278,219 A | 1/1994 | Lilley et al. | |
| 5,523,581 A | 6/1996 | Cadwalader | |
| 5,525,408 A | 6/1996 | Weir et al. | |
| 5,548,125 A | 8/1996 | Sandbank | |
| 5,604,784 A | 2/1997 | Widlicka et al. | |
| 5,857,007 A | 1/1999 | Haq | |
| 5,883,394 A * | 3/1999 | Mussman | 250/515.1 |
| 5,900,638 A * | 5/1999 | Jaeger et al. | 250/519.1 |
| 5,981,964 A * | 11/1999 | McAuley et al. | 250/515.1 |
| 6,048,379 A | 4/2000 | Bray et al. | |
| 6,105,578 A * | 8/2000 | Sommers et al. | 128/849 |
| 6,153,666 A | 11/2000 | Lagace | |
| 6,278,125 B1 * | 8/2001 | Belek | 250/519.1 |
| 6,320,938 B1 | 11/2001 | Hopper | |
| 6,456,684 B1 | 9/2002 | Mun et al. | |
| 6,481,888 B1 | 11/2002 | Morgan | |
| 6,653,648 B2 * | 11/2003 | Goldstein | 250/515.1 |
| 6,674,087 B2 | 1/2004 | Cadwalader et al. | |
| 6,740,260 B2 * | 5/2004 | McCord | 252/511 |
| 6,808,308 B2 * | 10/2004 | Thompson | 378/203 |
| 6,945,694 B2 | 9/2005 | Kantor et al. | |
| 6,967,343 B2 | 11/2005 | Batten et al. | |
| 7,099,427 B2 * | 8/2006 | Cadwalader et al. | 378/4 |
| 7,303,334 B2 * | 12/2007 | Cadwalader et al. | 378/203 |
| 7,391,042 B2 * | 6/2008 | Goldstein | 250/515.1 |
| 2005/0258404 A1 | 11/2005 | McCord | |

* cited by examiner

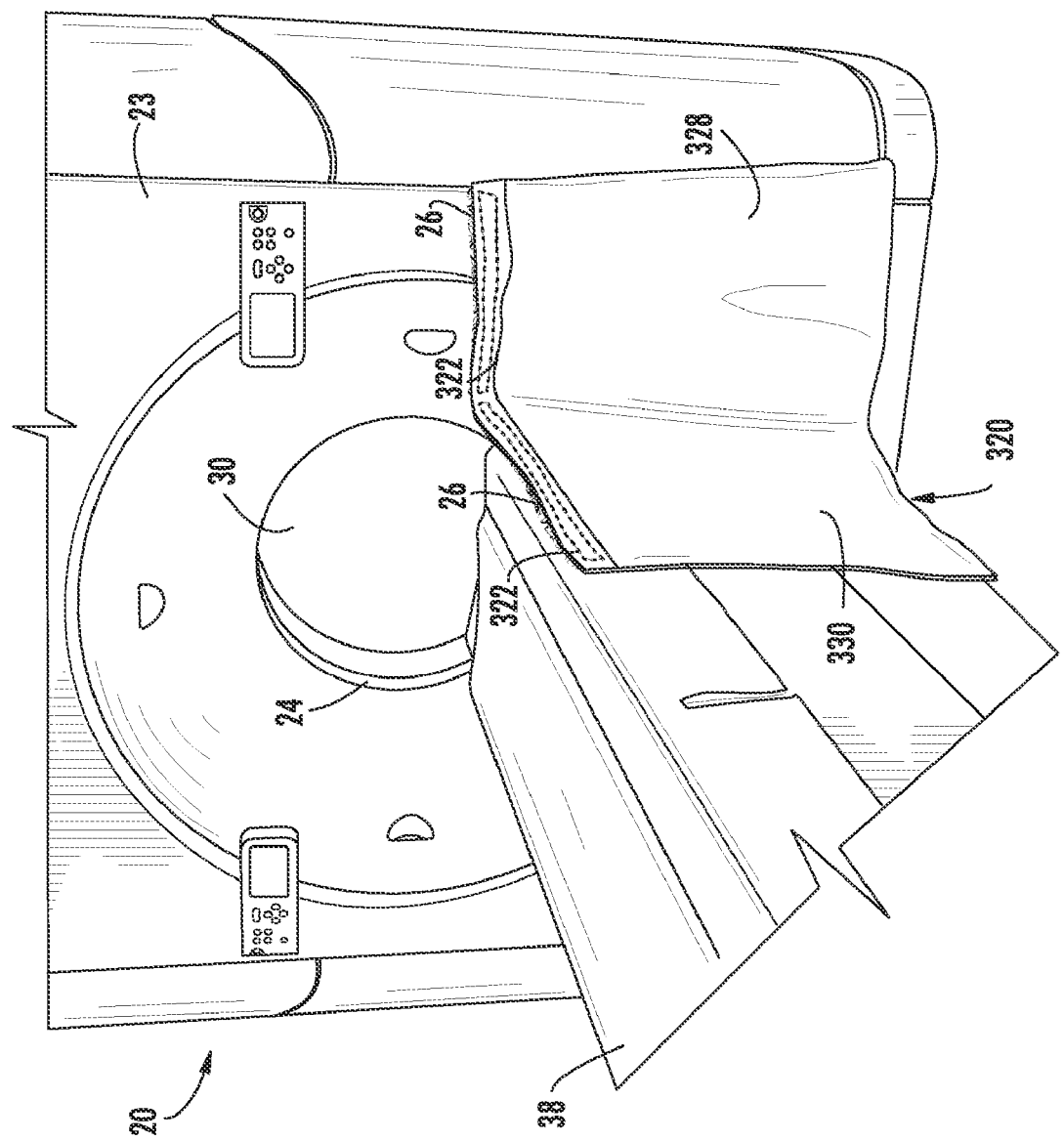

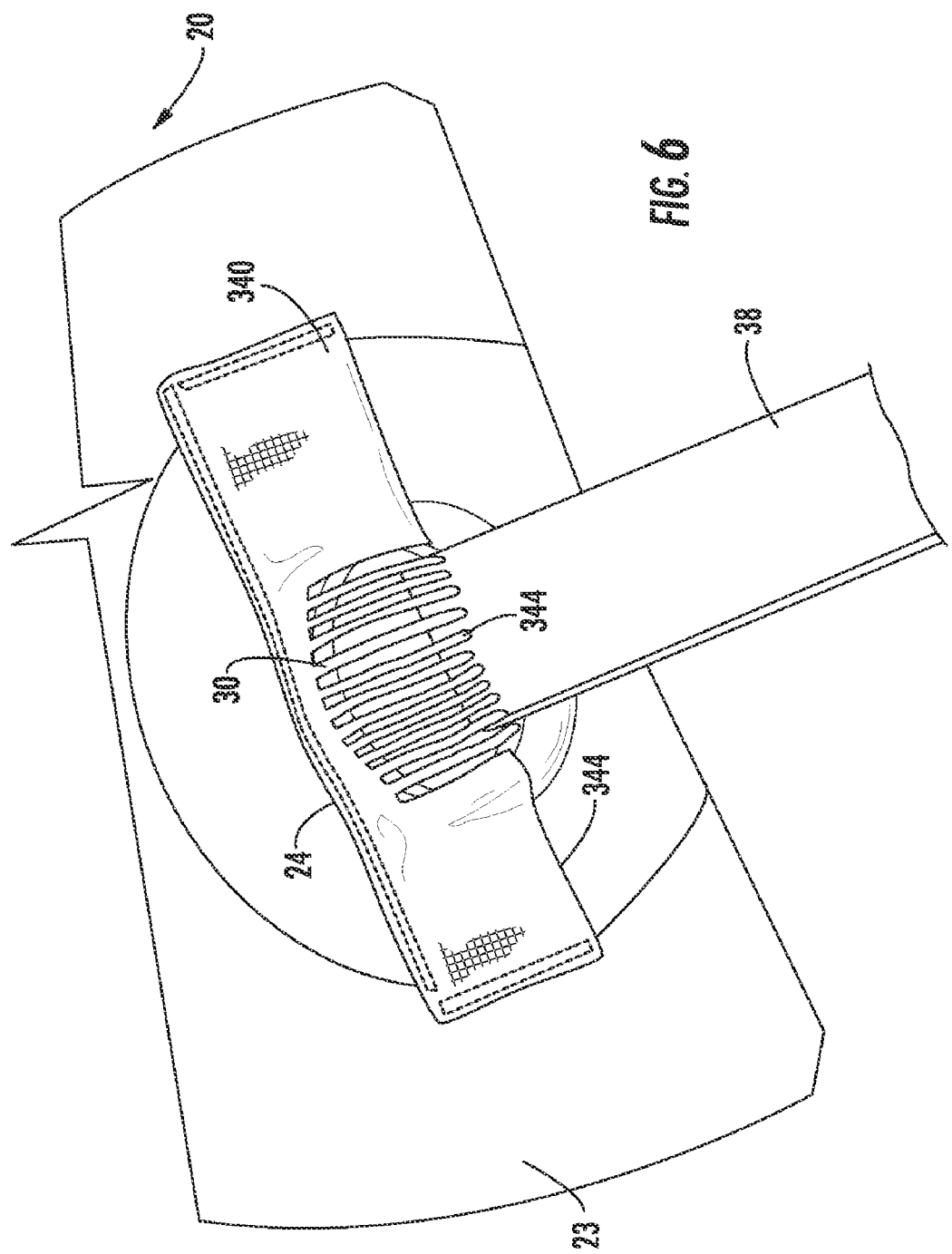

RADIATION ATTENUATION SYSTEM

CROSS-REFERENCE TO RELATED PATENT APPLICATIONS

The present application is a continuation of U.S. patent application Ser. No. 10/999,116, filed Nov. 29, 2004, now U.S. Pat. No. 7,303,334, which is a continuation-in-part of U.S. patent application Ser. No. 10/808,731, filed Mar. 25, 2004, now U.S. Pat. No. 7,099,427, the full disclosures of which are hereby incorporated by reference herein.

BACKGROUND

The present disclosure relates to a radiation attenuation system. More particularly, the present disclosure relates to a radiation attention system adapted for use with Computed Tomography procedures such as Computed Tomography scanning procedures and Computed Tomography fluoroscopy procedures. The present disclosure further relates to radiation attenuation system that is intended to reduce radiation exposure to at least one of a patient and medical personnel during Computed Tomography procedures.

Computed Tomography (CT) procedures are commonly used to obtain cross-sectional images of the patient's body, including images of a patient's brain, lungs, heart, liver, bones, blood vessels, etc. CT procedures are often used to diagnose different kinds of diseases such as cancer, to plan radiation treatments and surgeries, and to guide physicians during biopsies and other invasive procedures.

CT procedures involve the use of CT machines that use x-ray radiation to obtain the cross-sectional images. In conducting a CT procedure, a patient is placed in the CT machine between an x-ray generating source and an x-ray detecting sensor. The CT machine delivers controlled amounts of x-ray radiation from the x-ray generating source to the portion of the patient's body being examined. The x-ray detecting sensor is positioned on the other side of the patient and captures the x-ray radiation passing through the body of the patient. The x-ray detecting sensor sends an output signal to a processor representative of the amount of x-ray radiation absorbed by the patient. The processor receives the output signal from the x-ray detecting sensor and processes the signal to create the cross-sectional images of the patient on a display.

As presently configured, areas in which CT procedures are conducted (i.e. CT areas) expose not only the patient to radiation, but also the physicians and other medical personnel that may be present during the procedure. In CT procedures, significant amounts of radiation may be scattered to the patient and to the physician, or other medical personnel in the CT area (i.e. scatter radiation). The likelihood of having radiation scattered to the physician or other medical personnel is increased for CT fluoroscopy guided interventional procedures during which the medical personnel is in the CT area during the scan.

In addition, medical personnel and patients may be exposed to radiation emanating through the body or housing of the CT machine during a CT procedure. CT machines generally include a housing (i.e., gantry) defining an opening in which a patient is placed during a CT procedure. While the x-ray generating source generally concentrates the emitted x-ray radiation to the area defined by the opening, it is possible for at least some x-ray radiation to pass through the housing of the CT machine. Radiation passing through the housing of the CT machine may be received by the patient and/or the medical personnel present during the CT procedure.

Exposure to radiation may create potential health concerns. Radiation specialists and government agencies recognize the potential health risks caused by ionizing radiation and have developed the principle of ALARA (As Low As Reasonably Achievable). The principle of ALARA requires that radiation levels be reduced to the greatest degree possible taking into account a reasonable cost and physical application.

Accordingly, it would be advantageous to provide a radiation attenuation system that may be used during CT procedures to minimize a patient's exposure to radiation. It would further be advantageous to provide a radiation attenuation system that reduces the amount of radiation exposure for medical personnel working in a CT area. It would also be advantageous to provide a radiation attenuation system that is relatively flexible and compliant, and adaptable for use with a variety of CT machines and CT procedures. It would also be advantageous to provide a radiation attenuation system that is disposable. It would also be advantageous to provide a radiation attenuation system that is sterilizible before use. It would also be advantageous to provide a radiation attenuation system that may be coupled to CT devices having different configurations. It would further be advantageous to provide a radiation attenuation system for protecting medical personnel that is suitable for use with CT fluoroscopy procedures where medical personnel may need to insert biopsy needles or other instrumentation without hindrance. It would also be advantageous to provide a radiation attenuation system which provides a relatively high degree of comfort to the user. It would further be advantageous to provide a radiation attenuation system that is configured to reduce the amount of radiation exposure realized by a patient and/or medical personnel due to radiation emanating from the body or housing of a CT machine. It would further be advantageous to provide a CT machine having a radiation attenuation system configured to minimize the amount of radiation that passes through the body or housing of the CT machine and into the CT area. It would still further be advantageous to provide a housing for a CT machine configured to minimize the amount of radiation that passes through the substrate or body of the housing into the CT area. It would be desirable to provide for a radiation attenuation system having one or more of these or other advantageous features.

SUMMARY

An exemplary embodiment relates to a system for the attenuation of radiation during a Computed Tomography procedure using a Computed Tomography machine having a gantry defining an opening configured to receive a patient table. The system includes a shield made of a flexible radiation attenuation material and an interface supporting the shield at the Computed Tomography machine. The interface allows the shield to be selectively added to and removed from the Computed Tomography machine.

Another exemplary embodiment relates to a method of attenuating radiation during a Computed Tomography procedure preformed by a Computed Tomography machine having a gantry defining an opening. The method includes selectively supporting a flexible radiation attenuation material at least partially in front of the opening defined by the gantry. The flexible radiation attenuation material is selectively addable to and removable from in front of the opening by the medical personnel depending on the Computed Tomography procedure.

Another exemplary embodiment relates a Computed Tomography machine. The Computed Tomography machine includes a gantry defining an opening through which a patient table is at least partially inserted during a Computed Tomography procedure and a housing enclosing the gantry without substantially covering the opening and remaining fixed relative thereto. The housing is at least partially defined by a front panel that is formed of a substrate and a radiation attenuation material. The radiation attenuation material is in the form of a flexible sheet and is fixed relative to the substrate. The radiation attenuation material attenuates radiation that would otherwise pass through the front panel during the Computed Tomography procedure.

BRIEF DESCRIPTION OF THE DRAWINGS

FIG. 5 is a perspective view of a radiation attenuation system according to another exemplary embodiment.

FIG. 6 is a perspective view of another radiation attenuation system according to another exemplary embodiment.

DETAILED DESCRIPTION

Figure 1:
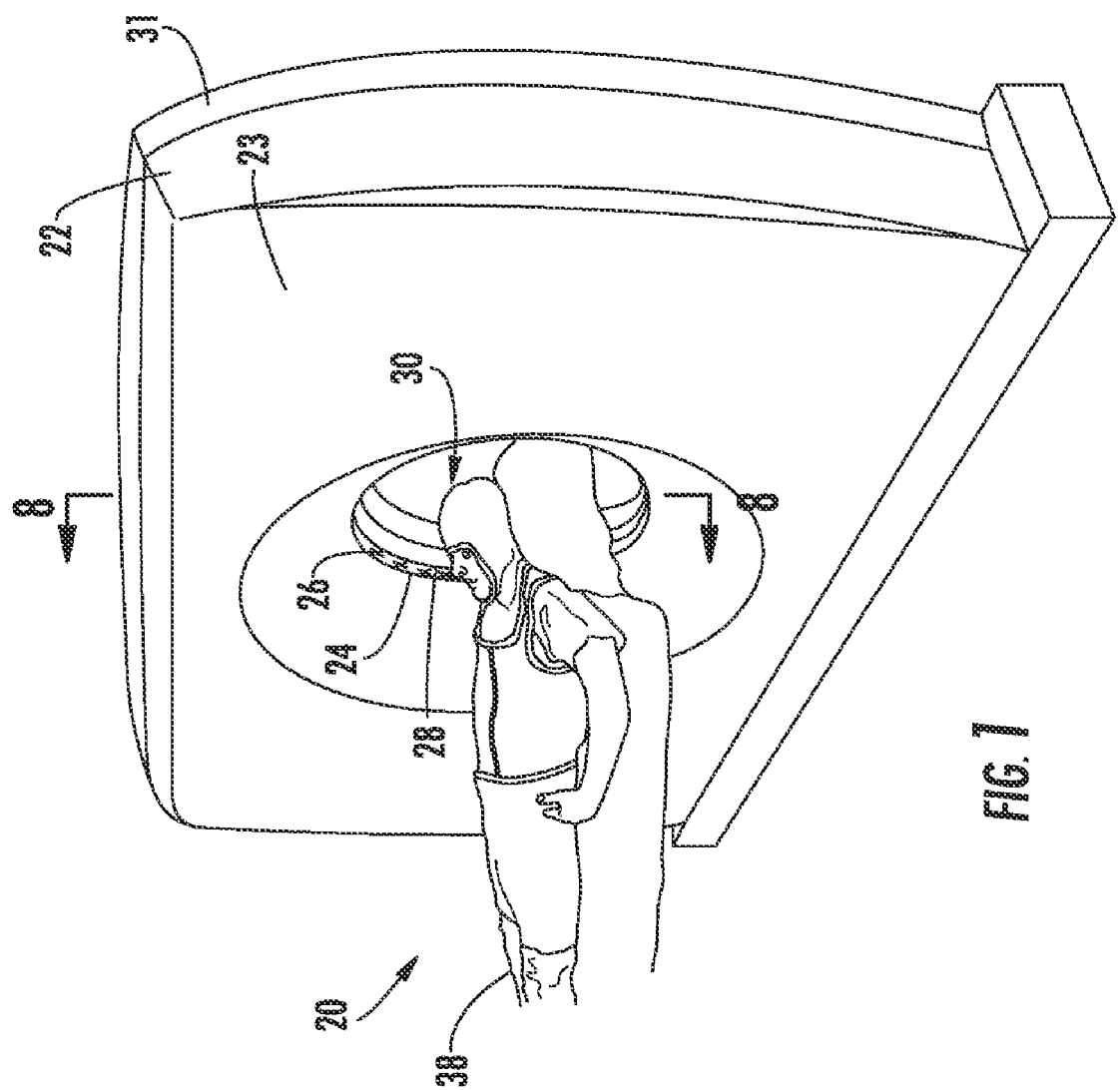
FIG. 1 is a perspective view of a radiation attenuation system for protecting a patient according to an exemplary embodiment.

FIG. 1 shows a Computed Tomography (CT) machine 20 of the type commonly used to create cross-sectional images the body of a patient 10. CT machines are well known and widely used in the medical field. Accordingly, CT machine 20, as illustrated, is intended to be representative of all conventionally known CT machines and is not intended to be limited to the exact configuration shown.

CT machine 20 may be used for both CT scanning procedures and CT fluoroscopy procedures. As used herein, the use of the term "CT scanning procedures" is intended to mean CT procedures conducted as part of a noninvasive examination during which a medical personnel 12 (e.g. a physician, nurse, technician, and the like) administering or otherwise involved with a CT procedure is likely to be outside of the area in which the CT procedure is conducted (i.e., the CT area). The term "CT fluoroscopy procedure", as used herein, is intended to mean CT procedures conducted as part of an invasive surgical procedure during which the medical personnel 12 is likely to remain in the CT area and substantially near the CT machine during the CT procedure.

CT machine 20 includes a housing 22 having a front side 23 and a back side 315. Housing 22 encloses a support structure, commonly referred to as gantry 24, that is configured to support at least one x-ray emitter 26 and at least one x-ray detector 28. Gantry 24 may support the x-ray emitter 26 and the x-ray detector 28 in a manner sufficient to allow for the orbital rotation of x-ray emitter 26 and x-ray detector 28 around patient 10. The gantry 24 defines an opening 30 in which at least a portion of patient 10 is inserted during the CT procedure. In its most common form, opening 30 is a generally circular opening. The illustration of opening 30 as a circular opening is not intended to limit the applicability of the present invention to CT machines having circular openings. As can be appreciated, the present invention is equally applicable with alternative CT machines having openings configured in any of a variety of shapes.

CT machine 20 further includes a patient table 38 configured to support the body of patient 10. Patient table 38 is generally positioned perpendicular to the front side 23 of housing 22 and may be movable in the vertical and horizontal directions relative to opening 30 as well as transversely. As can be appreciated, for alternative CT machines, patient table 38 may remain stationary and housing 22 may move relative to patient table 38.

To obtain an image, patient 10 is placed on patient table 38 and moved into opening 30 wherein patient 10 is positioned between x-ray emitter 26 and x-ray detector 28. A primary beam of x-ray radiation emanating from x-ray emitter 26 passes through patient 10 before being captured by x-ray detector 28. The x-ray radiation beam emanating from x-ray emitter 26 and passing through patient 10 is referred to herein as entrance radiation. During CT fluoroscopy procedures, wherein medical personnel 12 is standing near patient 10 and CT machine 20, medical personnel 12 may be inadvertently exposed to entrance radiation and radiation leakage from CT machine 20.

In addition to entrance radiation and radiation leakage, CT procedures are likely to generate scatter radiation. Scatter radiation refers to radiation emanating from x-ray emitter 26 that reflects off of and through an object such as patient 10, CT machine 20, the floor in CT area, etc. and scatters throughout the CT area. During a typical CT scanning procedure, the only person likely to be exposed to scatter radiation is patient 10. However, during CT fluoroscopy procedures, or any other CT scanning procedure in which medical personnel 12 remain in the CT area, medical personnel 12 may also be exposed to scatter radiation. As explained above, exposure to radiation may create a health risk and should be reduced whenever practicably possible.

Figure 2:
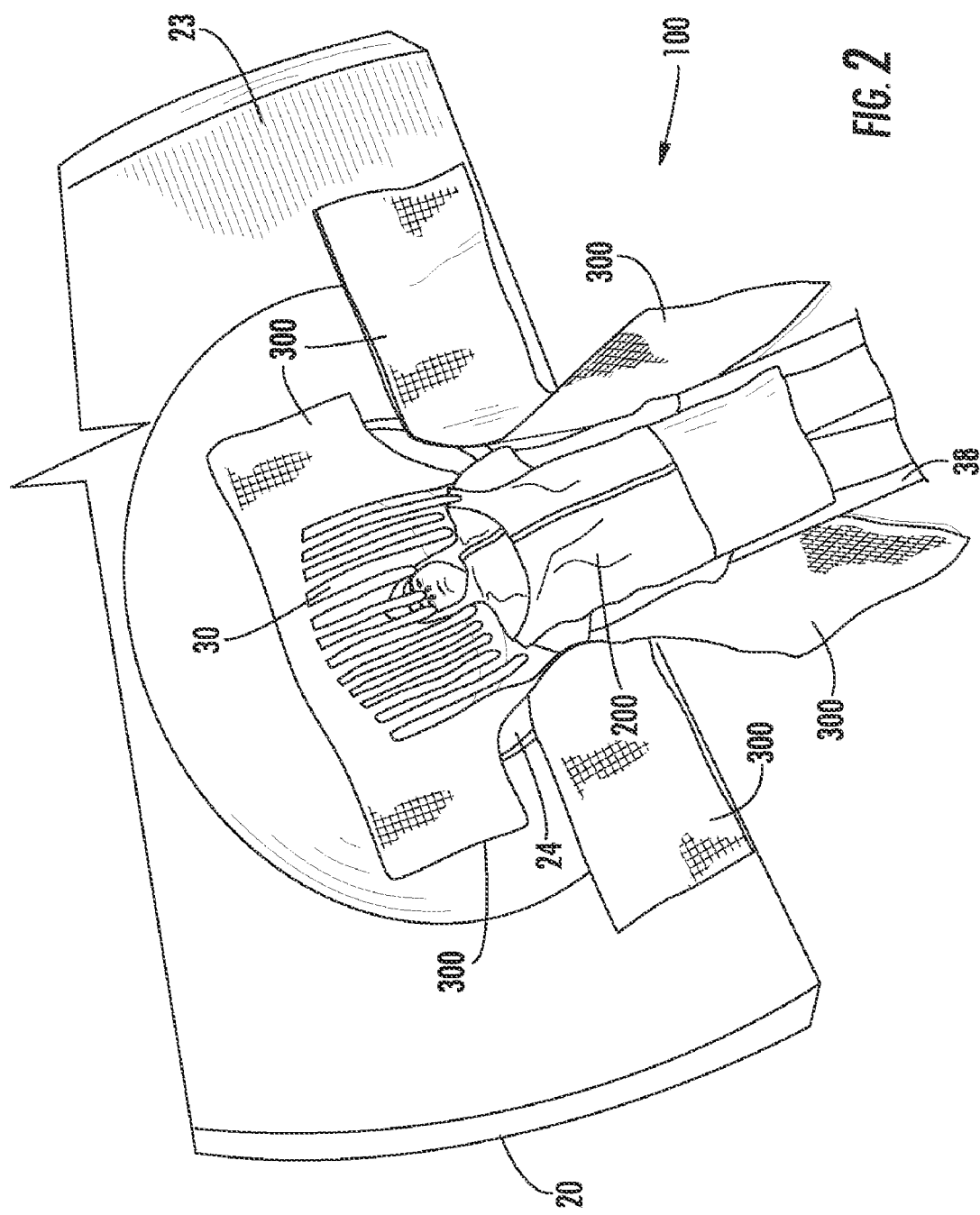
FIG. 2 is a perspective view of a radiation attenuation system for protecting at least one of a patient and a medical personnel according to an exemplary embodiment.

Referring to FIG. 2, a radiation attenuation system 100 configured to minimize radiation exposure during a CT procedure is shown. Radiation attenuation system 100 includes a first radiation attenuation system 200 that is intended to assist in the protection of patient 10 from unnecessary exposure to radiation during a CT procedure and a second radiation attenuation system 300 that is intended to assist primarily in the protection of medical personnel 12 from exposure to radiation during a CT procedure. According to an exemplary embodiment, radiation attenuation system 100 may further include a third radiation attenuation system 400 that is intended to reduce radiation exposure to at least one of a patient and the medial personnel during a CT procedure. First radiation attenuation system 200, second radiation system 300, and third radiation system 400 include at least one radiation barrier article for reducing radiation exposure. Depending on the CT procedure being performed, first radiation attenuation system 200, second radiation attenuation system 300, and third radiation system 400 may be used in any of a variety of combinations, or alternatively may be used separately as individual radiation attenuation systems.

During a CT procedure, patient 10 must be exposed to x-ray radiation (i.e. entrance radiation) in order for cross-sectional images of the patient's body to be obtained. CT procedures are often focused on a specific portion of the patient's body (i.e. the target area). While the target area must be exposed to entrance radiation, the surrounding portions of the patient's body (i.e. secondary areas) do not have to be exposed. Radiation attenuation system 200 is intended to minimize a patient's exposure to entrance radiation, radiation leakage and scatter radiation present during a CT procedure by shielding the secondary areas.

Figure 3A:
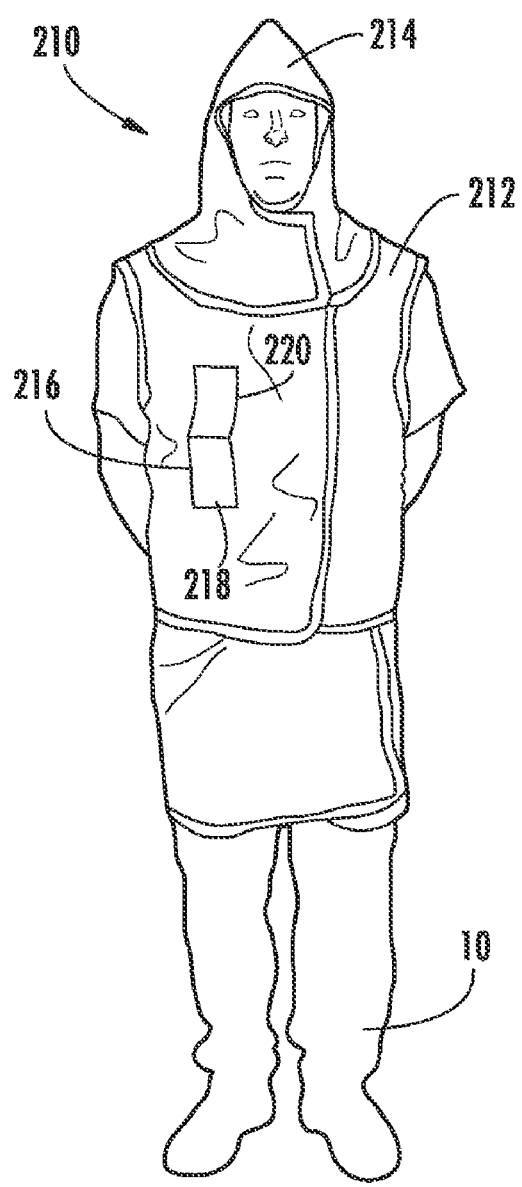
FIG. 3a is an anterior view of a patient wearing radiation attenuating garment according to exemplary embodiment.
Figure 3B:
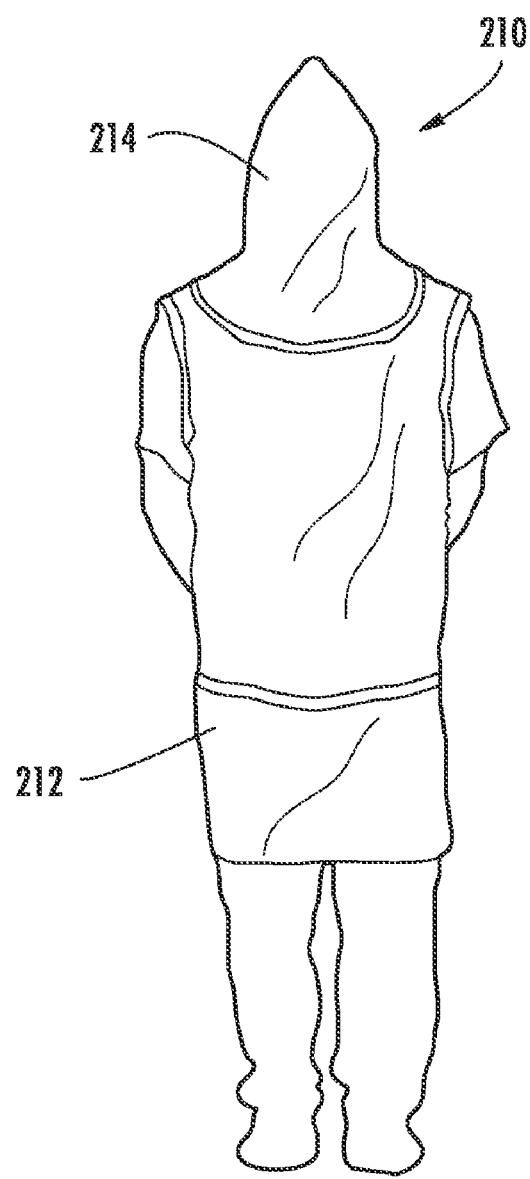
FIG. 3b is a posterior view of a patient wearing radiation attenuating garment according to exemplary embodiment.

Referring to FIG. 3, radiation attenuation system 200 includes a radiation attenuation wrap, shield, cloth, or garment 210. Garment 210 may be useful in blocking or attenuating radiation, and assisting in the protection of patient 10. Garment 210 may be made of any radiation attenuation material and preferably is made of a light-weight and flexible radiation attenuation material. Preferably garment 210 is made of a radiation attenuation material that provides a relatively high degree of comfort to the patient. Garment 210 may used to cover the portions of patient 10 during a CT procedure that are not going to be examined.

Garment 210 preferably includes a body cover portion 212 and a head cover (e.g. hood, hat, helmet, etc.) portion 214. Body cover portion 212 is not limited covering a patient's torso and may be configured to include leg cover portions, foot cover portions, arm cover portions, and hand cover portions. Preferably, garment 210 wraps around (e.g. underneath) patient 10 and does not simply drape over the top of patient 10. Head cover portion 214 is intended to protect a patient's head from radiation exposure, and may include portions covering a patient's face, forehead and neck. As can be appreciated, the configuration of garment 210 may vary depending on the application and portion of the patient's body that is to be scanned. For example, it would be anticipated that garment 210 would be configured differently for scanning of the chest as compared to the abdomen or an extremity. Garment 210 may be made in range of sizes to fit adult or adolescent patients as well as infants.

Garment 210 may include a fenestration area 216 for providing access to the target area (i.e. the portion of the patient's body to be scanned) through an aperture (shown as an rectangular strip 218). Fenestration area 216 further provides an opening for allowing medical personnel 12 to access patient 10 for conducting various invasive procedures, such as the fluoroscopic guidance and/or manipulation of instruments during surgical procedures. According to a preferred embodiment, fenestration area 216 may be selectively sealed or opened by coupling a fastener 220 to garment 210 near fenestration area 216. According to a particularly preferred embodiment, a hook and loop fastener is coupled to garment 210 and allows fenestration area 216 to be selectively sealed or opened depending on the CT procedure being conducted.

According to a particularly preferred embodiment, garment 210 is configured as a combination of a skirt, a vest, and a helmet. Such a configuration may be particularly suitable for procedures wherein the target area is the patient's abdomen or chest area. During a procedure of a patient's abdomen or chest, medical personnel can access the target area by moving a portion of the vest upwards to expose the desired area. However, the garment 210 is not limited to such a configuration, and such a garment could be used for procedures wherein the target area is not the patient's abdomen or chest.

While garment 210 is shown as an attenuation system that may be useful during CT procedures to protect a patient from radiation exposure, garment 210 is equally applicable with any procedure that emits ionizing radiation such as, but not limited to, intraoperative use of radiation equipment and implanting radiation therapy devices into patients that emit radiation.

As stated above, physicians, nurses, technicians, and other health care employees (collectively referred to as medical personnel) present during a CT procedure may be exposed radiation. Medical personnel present for numerous CT procedures may be exposed to significant cumulative radiation doses over time. Radiation attenuation system 300 is intended to reduce radiation exposure to medical personnel 12 present in the CT area during a CT procedure. Radiation attenuation system 300 may be particularly applicable with CT fluoroscopy procedures wherein medical personnel 12 is likely to be near the primary beam of x-ray radiation emanating from the CT machine or at least in an area susceptible to secondary scattered radiation or radiation leakage.

Radiation attenuation system 300 includes at least one radiation barrier article coupled substantially near or to CT machine 20 configured to reduce radiation exposure to medical personnel 12. For purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

Figure 4:
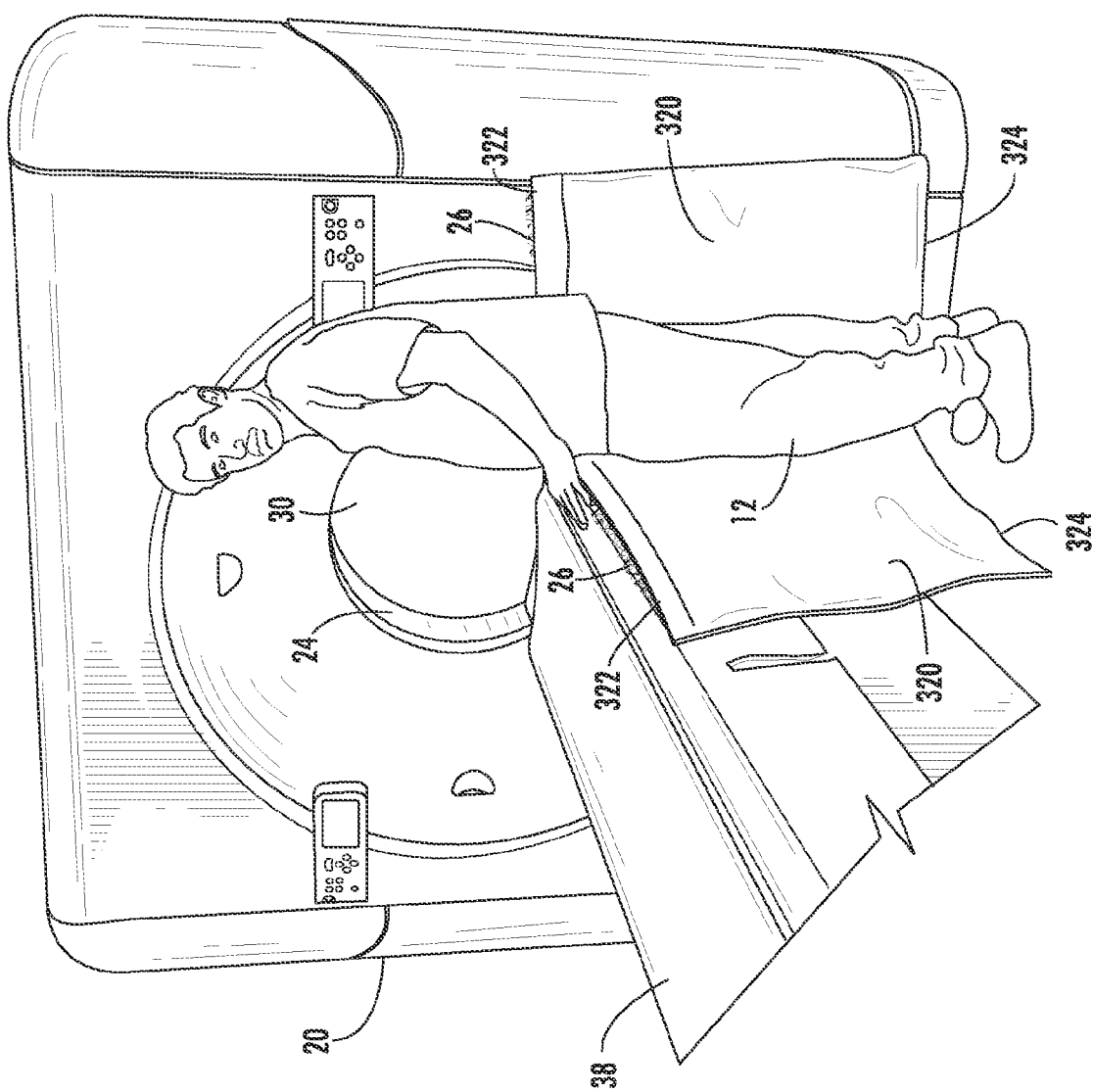
FIG. 4 is a perspective view of a radiation attenuation system according to another exemplary embodiment.

Referring to FIG. 4, radiation attenuation system 300 may include a first radiation panel, shield, or pad 320 that may be useful in blocking or attenuating radiation, and assisting in the protection of medical personnel 12. Pad 320 is made of a radiation attenuation material and is positioned between CT machine 20 and medical personnel 12. Pad 320 may be coupled near or to the CT machine 20. Preferably, pad 320 is substantially rectangular shape having an outer edge that includes a top edge 322 and an opposite bottom edge 324.

Pad 320 may be coupled near or to CT machine in any position that may protect medical personnel 12 and/or patient 10 from unintentional radiation exposure. According to an exemplary embodiment, pad 320 is coupled to the side of patient table 38. Pad 320 is coupled near the top surface of patient table 38 and hangs, extends, or drapes over the side of patient table 38 so that bottom edge 324 is near the floor of the CT area. Depending on the size of pad 320 and patient table 38, multiple pads 320 may be coupled to patient table 38 in order to provide sufficient protection for medical personnel 12. According to a second exemplary embodiment, pad 320 is coupled to the front side 23 of CT machine 20. Pad 320 is coupled near gantry 24 substantially tangential to the bottom of opening 30 and extends downward so that bottom edge 324 is near the floor. Bottom edge 324 may be weighted in order to urge bottom edge 324 in the direction of the floor and help maintain pad 320 in a protective position. As can be appreciated, pad 320 is suitable for use anywhere in the CT area so long as pad 320 is between CT machine 20 and medical personnel 12.

According to a preferred embodiment, shown in FIG. 5, pad 320 is a flexible member sized to span across both the areas covered by the first and second exemplary embodiments described above. For such an embodiment, pad 320 may be described as having two portions, a first panel 328 that is integrally formed with a second panel 330. First panel 328 is coupled to the front side 23 of CT machine 20 near gantry 24 and second panel 330 is coupled to a side portion of patient table 38 that is near opening 30. Pad 320 is positioned between CT machine 20 and medical personnel 12. First panel 328 and second panel 330 conform to the contour of CT machine 20 and are substantially perpendicular to each other. As previously stated, bottom edge 324 may be weighted. Such a configuration is intended to reduce the amount of radiation exposure experienced by medical personnel 12 while enabling medical personnel 12 to remain substantially close to opening 30 and patient 10.

Referring to FIGS. 4 and 5, to couple pad 320 to CT machine 20, pad 320 may include a fastener 326. According to a preferred embodiment, fastener 26 allows for the detachable coupling of pad 320 to CT machine 20. According to a particularly preferred embodiment, pad 320 includes a hook and loop fastener coupled to the outer edge of pad 320 for allowing the detachable coupling of pad 320 to CT machine 20. As shown in FIGURES, fastener 26 is coupled to top edge 322. In alternative embodiments, fastener 26 may be coupled anywhere along the outer edge of pad 320, or anywhere else along pad 320. As can be appreciated, a number of suitable fasteners may provide the detachable coupling of pad 320 to CT machine 20 in addition to hook and loop fasteners such as, snaps, grommets, adhesives, zippers, etc.

Preferably, pad 320 is coupled to CT machine 20 and patient table 38 on both sides of patient table 38 as shown in FIG. 2. If pad 320 includes a detachable fastener 26, a single pad 320 can be utilized by selectively positioning pad 320 along CT machine 20 and patient table 38 to protect medical personnel 12. As can be appreciated, pad 320 may be dimensioned and shaped in any of a variety of ways depending on the application. For example, pad 320 may be configured in any of a variety of shapes such as a pad having a curvilinear portion to more readily conform to a CT machine.

Referring to FIG. 6, radiation attenuation system 300 may also include a second radiation barrier article, shown as radiation curtain, shield, or drape 340. Drape 340 may be useful in blocking or attenuating radiation, and assisting in the protection of medical personnel 12. Drape 340 is intended to be positioned between CT machine 20 and medical personnel 12. Drape 340 is coupled near gantry 24 of CT machine 20 and substantially covers opening 30. Drape 340 may be made of any attenuation material and is intended to reduce the amount of entrance radiation, radiation leakage and scatter radiation that medical personnel 12 or patient 10 may be exposed to during a CT procedure. In its most preferred form, drape 340 is a made of a flexible attenuation material having an outer edge that includes a bottom edge 344 that hangs downward from a top edge. Preferably, bottom edge 344 drapes around patient 12 and conform to the patient's body and patient table 38. Similar to pad 320, drape 340 may include a fastener, such as a hook and loop fastener, along the outer edge and may further be weighted along bottom edge 344 to maintain a desired position.

Figure 7A:
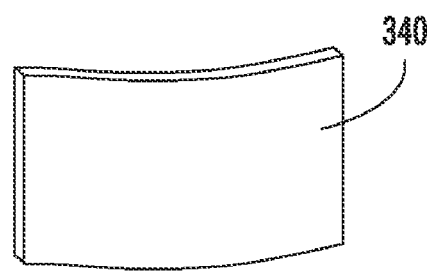
FIG. 7a is a plan view of a radiation attenuation pad according to an exemplary embodiment.

According to an exemplary embodiment, drape 340 is a solid shield or member covering opening 30 (shown in FIG. 7*a*). Configuring drape 340 as a solid member may be particularly useful during CT scanning procedures during which medical personnel 12 do not need access to the portion of the patient's body being scanned. Drape 340 may include a viewing panel (shown as a window 346 in FIG. 7*b*) that is relatively clear or translucent for the viewing of patient 12 within CT machine 20. Window 346 may be of a variety of shapes and sizes, which may be dictated at least in part by the particular application.

Figure 7E:
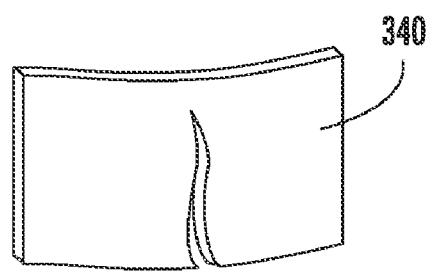
FIG. 7e is a plan view of a radiation attenuation pad according to an exemplary embodiment.
Figure 7B:
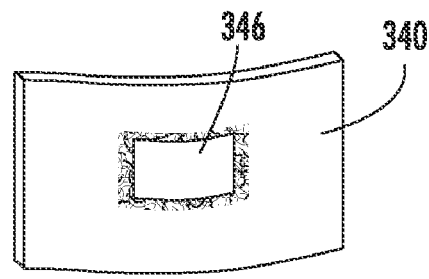
FIG. 7b is a plan view of a radiation attenuation pad according to an exemplary embodiment.
Figure 7F:
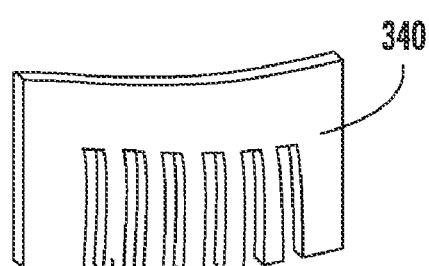
FIG. 7f is a plan view of a radiation attenuation pad according to an exemplary embodiment.
Figure 7C:
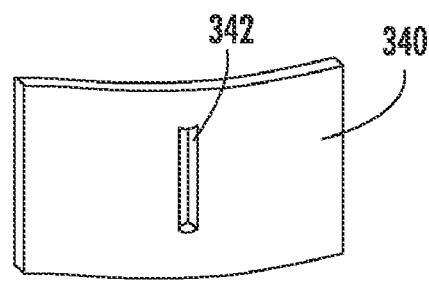
FIG. 7c is a plan view of a radiation attenuation pad according to an exemplary embodiment.
Figure 7G:
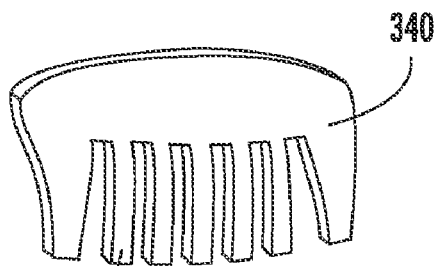
FIG. 7g is a plan view of a radiation attenuation pad according to an exemplary embodiment.
Figure 7D:
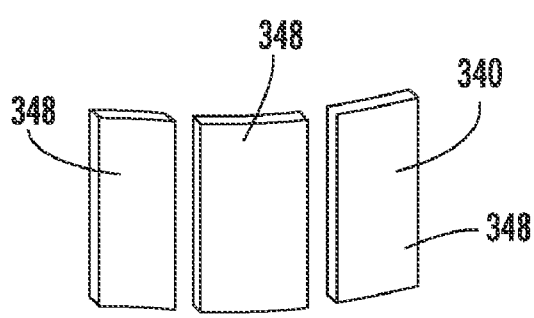
FIG. 7d is a plan view of a radiation attenuation pad according to an exemplary embodiment.

To accommodate CT procedures during which it would be desirable for medical personnel 12 to access the portion of the patient's body being scanned, drape 340 may include a fenestration area 342 for providing access to the portion of the patient that is within CT machine 20 during the CT procedure. Fenestration area 342 may be an aperture (shown as a rectangular opening in FIG. 7*c*) that allows medical personnel 12 to insert medical instrumentation when conducting various invasive procedures, such as the fluoroscopic guidance and/or surgical procedures. According to a preferred embodiment, shown in FIG. 7*d*, drape 340 may be configured as a plurality of flaps 348 which do not substantially restrict medical personnel 12 from accessing patient 10. According to an alternative exemplary embodiment, as shown in FIG. 7*e*, drape 340 is a solid member having a slit or cut extending from the bottom edge in a substantially vertical direction to define flaps 348 thereby providing access to patient 10. According to a particularly preferred embodiment, drape 340 is a solid barrier having a plurality of slits formed in a substantially vertical direction to define flaps 348 (shown in FIG. 7*f*). The use of flaps 348 in combination with drape 340 is intended to reduce the radiation exposure experienced by medical personnel 12 without substantially restricting access to patient 10.

Figure 7H:
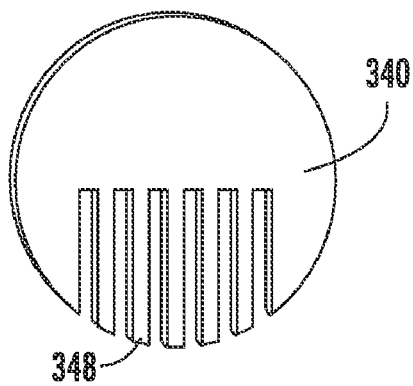
FIG. 7h is a plan view of a radiation attenuation pad according to an exemplary embodiment.

As shown in FIGS. 7*a*-7*f*, drape 340 is a generally rectangular shield that is disposed across opening 30. As can be appreciated, drape 340 may be dimensioned and shaped in any of a variety of ways depending on the CT machine and the application. For example, drape 340 may be configured in any of a variety of shapes such as a shield having a curvilinear portion to more readily conform to a CT machine (shown in FIG. 7*g*). Alternatively, drape 340 may be configured as having a circular shape (shown in FIG. 7*h*).

According to a preferred embodiment, as shown in FIG. 2, radiation attenuation system 300 includes the use of both pad 320 and drape 340 to assist in the protection of patient 10 and medical personnel 12. The combination of pad 320 and drape 340 may increase the level of protection relative to the use of any one of the articles alone. The radiation barrier articles of radiation attenuation system 300 (i.e. pad 320 and drape 340)

may be selectively positionable to allow medical personnel 12 to move an article out of the way if the article is not needed.

FIGS. 8 through 13 illustrate an attenuation system 400 configured to attenuate radiation emanating through housing 22 of CT machine 20 during a CT procedure. As detailed above, during a CT procedure, radiation is applied to patient 10 by x-ray emitter 26 which is supported by gantry 24. During the procedure, it is possible for a percentage of radiation being applied by x-ray emitter 26 to inadvertently pass through housing 22 rather than being applied solely to patient 10. Accordingly, attenuation system 400 is intended to protect patient 10 and/or medical personnel 12 from being undesirably exposed to radiation emanating through housing 22 and into the CT area.

As can be appreciated, the characteristics of CT machine 20 and housing 22 (e.g., shape, number of components, material, wall thickness, size, etc.) may vary depending on a number of factors including factors relating to the function of CT machine 20, materials used to build CT machine 20, and/or the aesthetics of CT machine 20. It should be clearly understood that attenuation system 400 is suitable for use with any CT machine having a housing through which radiation (e.g., primary beam, scatter, etc.) may undesirably emanate from during a CT procedure. Attenuation system 400 can also be used with other types of radiation systems, such as diagnostic x-ray equipment.

Housing 22 is shown as being a generally continuous member (e.g., panel, partition, support, etc.), but according other suitable embodiments, may be configured as a plurality of members coupled together to define housing 22. Housing 22 is defined by a substrate (e.g., body, etc.) having a first surface 23, shown as being an outer surface (e.g., exposed surface, etc.), and a second surface 25, shown as being an inner surface (e.g., concealed surface, etc.).

Attenuation system 400 includes at least one radiation barrier (e.g., member, panel, liner, etc.), shown as radiation shield 410. Radiation shield 410 may be provided as an inner, outer, or intermediate surface of housing 22. According to one exemplary embodiment (shown in FIG. 8), radiation shield 410 is shown as being supported adjacent to second surface 25 of housing 22. According to another exemplary embodiment, radiation shield 410 is shown as being supported adjacent to first surface 23 of housing 22 (shown in FIG. 9).

Figure 13:
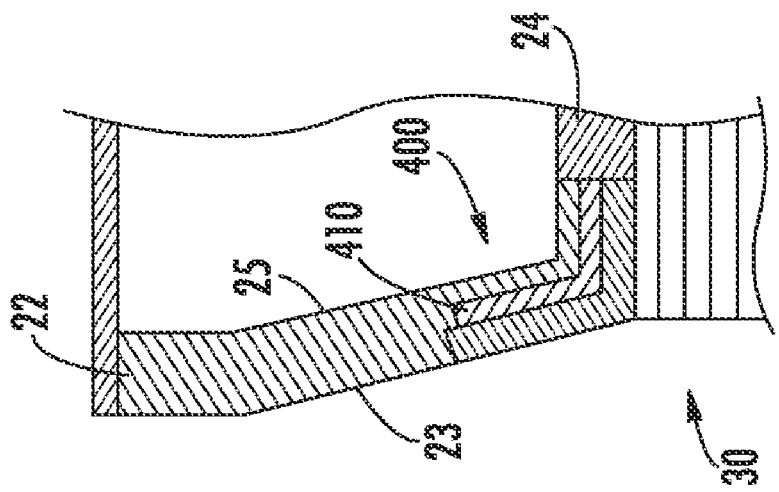
FIG. 13 is a partial cross-sectional view of the CT machine of FIG. 1, taken along line 8-8 showing the housing according to another exemplary embodiment.
Figure 12:
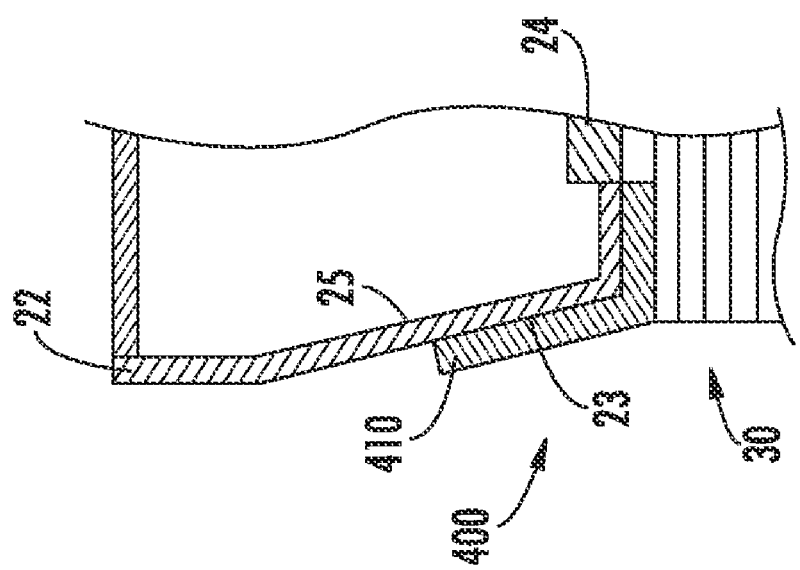
FIG. 12 is a partial cross-sectional view of the CT machine of FIG. 1, taken along line 8-8 showing the housing according to another exemplary embodiment.
Figure 11:
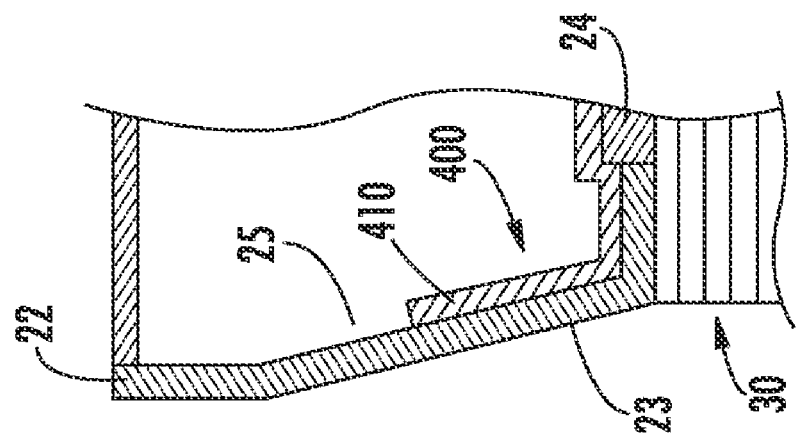
FIG. 11 is a partial cross-sectional view of the CT machine of FIG. 1, taken along line 8-8 showing the housing according to another exemplary embodiment.

Radiation shield 410 may cover substantially all of second surface 25 and/or first surface 23 of housing 22, or alternatively, may be selectively provided in areas where radiation is likely to emanate housing 22 (e.g., near gantry 24, etc.), as shown in FIGS. 11 through 13. The addition of radiation shield 410 to CT machine 20 reduces the amount of radiation emanating through housing 22 during a CT procedure. Reducing the amount of radiation emanating through housing 22 is intended to reduce the radiation exposure of patient 10 and/or medical personnel 12 present during the CT procedure.

Radiation shield 410 may be supported relative to housing 22 in a variety of configurations. For example, radiation shield 410 may be coupled (directly or indirectly) to housing 22. The coupling of radiation shield 410 to housing 22 may be accomplished using a variety of suitable techniques including, but not limited to, adhesives, mechanical fasteners (e.g., clips, snaps, hook and loop fasteners, etc.) any suitable welding process (e.g., ultrasonic welding, etc.), painting, embedding, spraying, etc. Any of the just mentioned coupling techniques may be used alone or in combination to couple radiation shield 410 to housing 22. According to other suitable embodiments, radiation shield 410 may not be coupled to housing 22, but instead may be supported by a supplemental member (e.g., a structural component of CT machine 20, a portion of gantry 24, etc.) and/or provided as a filler between x-ray emitter 26 and housing 22.

Figure 10:
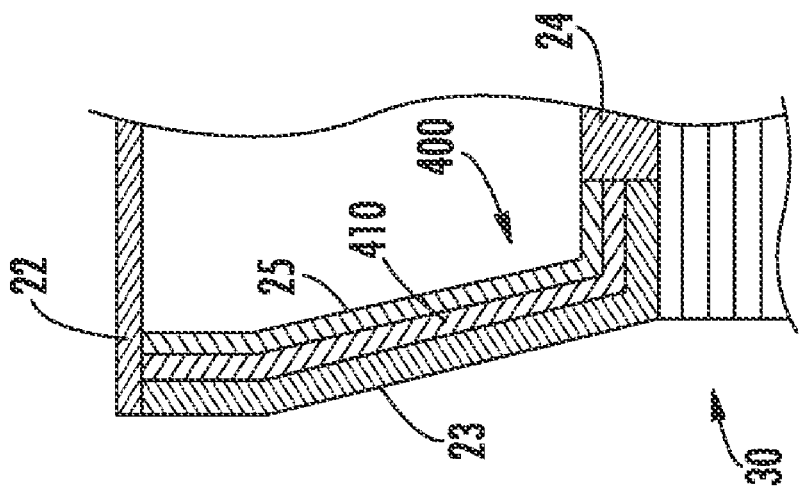
FIG. 10 is a partial cross-sectional view of the CT machine of FIG. 1, taken along line 8-8 showing the housing according to another exemplary embodiment.
Figure 9:
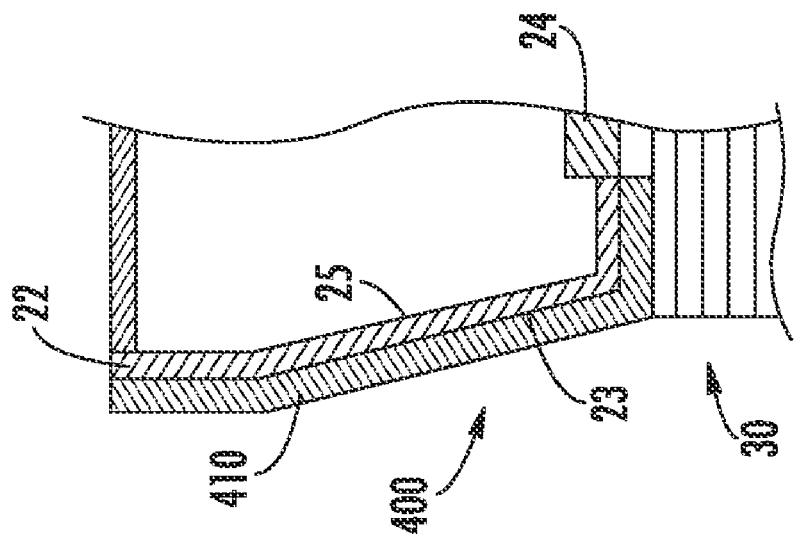
FIG. 9 is a partial cross-sectional view of the CT machine of FIG. 1, taken along line 8-8 showing the housing according to another exemplary embodiment.
Figure 8:
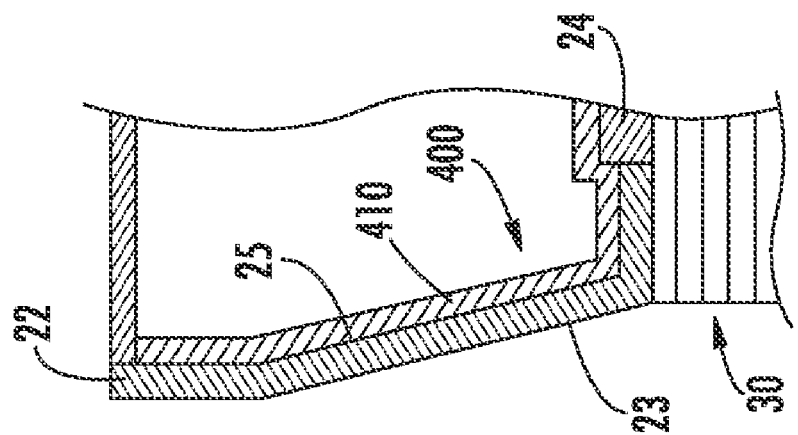
FIG. 8 is a partial cross-sectional view of the CT machine of FIG. 1, taken along line 8-8 showing the housing according to one exemplary embodiment.

FIG. 10 shows attenuation system 400 according to another suitable embodiment. In such an embodiment, housing 22 includes multiple layers and radiation shield 410 is disposed (e.g., sandwiched, etc.) between (e.g., intermediate, etc.) the layers. According to another embodiment, radiation shield 410 is integrally formed with housing 22. For example, housing 22 may be formed using a molding process in which the material used to form housing 22 is provided around radiation shield 410. Radiation shield 410 may be provided as a sheet-like member or alternatively may be provided as relatively small particles that is dispersed within the material used to form housing 22.

Each of the barrier articles of radiation attenuation system 100, including shield 410, described above may be made of any radiation attenuation material including, but not limited to, bismuth, barium, lead, tungsten, antimony, copper, tin, aluminum, iron, iodine, cadmium, mercury, silver, nickel, zinc, thallium, tantalum, tellurium, and uranium. Anyone of the aforementioned attenuation materials alone or in a combination of two or more of the attenuation materials may provide the desired attenuation. According to various exemplary embodiments, the articles of radiation attenuation system 100 can be made of the attenuation material disclosed in U.S. Pat. Nos. 6,674,087, 4,938,233, or 6,310,355 which are hereby incorporated by reference. However, the articles of radiation attenuation system 100 are not limited to such embodiments and may be made of any radiation attenuation material.

The degree of radiation transmission attenuation factor by the radiation attenuation material may be varied depending upon the specific application. According to an exemplary embodiment, the radiation attenuation material will have a radiation transmission attenuation factor of a percent (%) greater than about 50%, suitably greater than about 90%, suitably greater than about 95% of a 90 kVp beam.

Preferably, the radiation attenuation material is generally light and flexible, to maximize workability for processing, bending, folding, rolling, shipping, etc. The material may be formable (e.g. deformable) or compliant, and relatively "stretchable" (e.g. elastic). According to alternative embodiments, the material used may be generally rigid and inflexible, and/or substantially weighted.

According to a preferred embodiment, the articles of radiation attenuation system 100 are generally disposable in whole or in part, thereby minimizing ancillary sources of contamination that may arise from multiple uses. According to another suitable embodiment, the articles of radiation attenuation system 100 are generally non-toxic, recyclable, and/or biodegradable. According to an alternative embodiment, the articles of radiation attenuation system may be reusable (e.g. for attenuation of radiation from atomic/nuclear disaster, clean up, rescue operations, etc.). According to a preferred embodiment, the articles of radiation attenuation system may be sterilized between uses to minimize the likelihood of bacteriological or virus contamination. Sterilization may be performed in any convenient manner, including gas sterilization and irradiation sterilization.

The construction and arrangement of the articles of the radiation attenuation system as shown in the preferred and other exemplary embodiments is illustrative only. Although only a few embodiments of the present inventions have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, shield 410 may be configured in a variety of ways (e.g. depending on geometric requirements of housing 22.) depending on the application. Further, shield 410 may be configured as screens or curtains that are coupled within CT machine 20.

Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the present inventions as expressed in the appended claims.

What is claimed is:

1. A system for the attenuation of radiation during a Computed Tomography procedure using a Computed Tomography machine having a gantry defining an opening configured to receive a patient table, the system comprising:
    a shield made of a flexible radiation attenuation material, the flexible radiation attenuation material being sized to substantially cover the entire opening of the gantry; and
    an interface for supporting the shield in front of the opening of the gantry, the interface being part of the shield and comprising at least one of a hook and loop fastener, a snap, an adhesive, a grommet, or a zipper.

2. The system of claim 1, wherein the shield is a one-piece member extending continuously between a first portion configured to receive the interface and a second portion configured to drape over a patient undergoing the Computed Tomography procedure.

3. The system of claim 2, wherein the first portion of the shield remains substantially stationary as a patient enters the opening defined by the gantry.

4. The system of claim 3, wherein the second portion of the shield is configured to be engaged by the patient entering the opening.

5. The system of claim 1, wherein the flexible radiation attenuation material is a solid member.

6. The system of claim 1, wherein the flexible radiation attenuation material has a least one slit extending from a bottom edge in a substantially vertical direction that forms a flap in the shield.

7. The system of claim 1, wherein the flexible radiation attenuation material defines an aperture.

8. The system of claim 7, wherein the aperture is covered by a relatively clear viewing panel.

9. The system of claim 1, wherein the radiation attenuation material is substantially non-lead.

10. The system of claim 1, wherein the shield is configured to be coupled to the Computed Tomography machine.

11. The system of claim 10, wherein the interface facilitates the coupling of the shield to the Computed Tomography machine.

12. The system of claim 10, wherein the shield is configured to be directly coupled to the Computed Tomography machine.

13. A system for the attenuation of radiation during a Computed Tomography procedure using a Computed Tomography machine having a gantry defining an opening configured to receive a patient table, the system comprising:
    a shield made of a flexible radiation attenuation material, the flexible radiation attenuation material being sized to substantially cover the entire opening of the gantry; and
    an interface for supporting the shield in front of the opening of the gantry, the interface allowing the shield to be directly coupled to the Computed Tomography machine, wherein the shield is configured to be selectively added to and removed from in front of the opening of the gantry of the Computed Tomography machine depending on the Computed Tomography procedure.

14. The system of claim 13, wherein the interface is part of the shield.

15. A method of attenuating radiation during a Computed Tomography procedure preformed by a Computed Tomography machine having a gantry defining an opening, the method comprising:
    selectively supporting a flexible radiation attenuation material at least partially in front of the opening defined by the gantry to substantially cover the entire opening of the gantry; and
    selectively adding and removing the flexible radiation attenuation material to and from in front of the opening depending on the Computed Tomography procedure.

16. The method of claim 15, wherein the step of supporting the radiation attenuation material at least partially in front of the opening defined by the gantry involves coupling the flexible radiation attenuation material directly to the Computed Tomography machine.

17. The method of claim 15, wherein the step of supporting the radiation attenuation material at least partially in front of the opening defined by the gantry involves using an interface received by an upper portion of the radiation attenuation material.

18. A Computed Tomography machine comprising:
    a gantry defining an opening through which a patient table is at least partially inserted during a Computed Tomography procedure;
    a housing enclosing the gantry without substantially covering the opening and remaining fixed relative thereto, the housing being at least partially defined by a front panel that is formed of a substrate and a radiation attenuation material, the radiation attenuation material is in the form of a flexible sheet and is fixed relative to the substrate,
    wherein the radiation attenuation material attenuates radiation that would otherwise pass through the front panel during the Computed Tomography procedure.

19. The Computed Tomography machine of claim 18, wherein the radiation attenuation material is integrally formed with the substrate.

20. The Computed Tomography machine of claim 18, wherein the radiation attenuation material is supported adjacent to the substrate.

21. The Computed Tomography machine of claim 18, wherein the front panel at least partially defines the opening through which the patient table is at least partially inserted.

* * * * *